United States Patent
Kim et al.

(10) Patent No.: US 10,143,292 B2
(45) Date of Patent: Dec. 4, 2018

(54) BEAUTY SHEET AND METHOD FOR MANUFACTURING SAME

(71) Applicant: AMOLIFESCIENCE CO., LTD., Seoul (KR)

(72) Inventors: Chan Kim, Gwangju (KR); Seung Hoon Lee, Paju-si (KR); Kyu Won Baek, Seoul (KR); Song Hee Koo, Seoul (KR)

(73) Assignee: AMOLIFESCIENCE CO., LTD., Seoul (KR)

( * ) Notice: Subject to any disclaimer, the term of this patent is extended or adjusted under 35 U.S.C. 154(b) by 0 days.

(21) Appl. No.: 15/506,957

(22) PCT Filed: Aug. 28, 2015

(86) PCT No.: PCT/KR2015/009097
§ 371 (c)(1),
(2) Date: Feb. 27, 2017

(87) PCT Pub. No.: WO2016/032297
PCT Pub. Date: Mar. 3, 2016

(65) Prior Publication Data
US 2017/0251789 A1    Sep. 7, 2017

(30) Foreign Application Priority Data

Aug. 28, 2014    (KR) ........................ 10-2014-0113221

(51) Int. Cl.
| | | |
|---|---|---|
| A45D 44/00 | (2006.01) |
| A45D 44/22 | (2006.01) |
| A61K 8/02 | (2006.01) |
| A61K 8/81 | (2006.01) |
| A61K 8/87 | (2006.01) |
| A61Q 17/04 | (2006.01) |
| A61Q 19/02 | (2006.01) |
| A61Q 19/08 | (2006.01) |
| B32B 5/02 | (2006.01) |
| B32B 27/12 | (2006.01) |
| B32B 27/40 | (2006.01) |
| D04H 1/728 | (2012.01) |
| A61F 13/12 | (2006.01) |
| A61Q 19/00 | (2006.01) |

(52) U.S. Cl.
CPC ........... *A45D 44/002* (2013.01); *A45D 44/22* (2013.01); *A61F 13/122* (2013.01); *A61K 8/0212* (2013.01); *A61K 8/8129* (2013.01); *A61K 8/8176* (2013.01); *A61K 8/87* (2013.01); *A61Q 17/04* (2013.01); *A61Q 19/00* (2013.01); *A61Q 19/02* (2013.01); *A61Q 19/08* (2013.01); *B32B 5/022* (2013.01); *B32B 27/12* (2013.01); *B32B 27/40* (2013.01); *D04H 1/728* (2013.01); *A45D 2200/1036* (2013.01); *B32B 2307/7166* (2013.01)

(58) Field of Classification Search
CPC ...... A45D 44/002; D04H 1/728; B32B 27/40; A61K 8/87
See application file for complete search history.

(56) References Cited

U.S. PATENT DOCUMENTS

2015/0272855 A1*  10/2015  Kim .................. A45D 34/04
424/401

FOREIGN PATENT DOCUMENTS

| | | |
|---|---|---|
| JP | 2013128743 | 7/2013 |
| KR | 1020140091449 | 7/2004 |
| KR | 200418839 | * 6/2006 |
| KR | 1020110080066 | 7/2011 |
| KR | 101371987 | 3/2014 |
| KR | 1020140052639 | 5/2014 |

OTHER PUBLICATIONS

Papakonstantinou, et al., title: Hyaluronic acid; Dermatoendocrinol., vol. 4(3), pp. 253-258, published Jul. 1, 2012. (Year: 2012).*
International Search Report—PCT/KR2015/009097 dated Nov. 16, 2015.

* cited by examiner

*Primary Examiner* — Yanzhi Zhang
(74) *Attorney, Agent, or Firm* — Cantor Colburn LLP (57) ABSTRACT

Provided are a cosmetic sheet including: a cosmetic layer configured in the form of a nanofiber web and melted by moisture by electrospinning a water-soluble polymer material and a functional material together; and a moisture retaining layer separably attached to the cosmetic layer and retaining the moisture of the cosmetic layer when wearing the cosmetic layer on the face and performing outdoor activities, to thus prevent moisture from drying out during the time the cosmetic layer is absorbed into the skin, when wearing the cosmetic sheet on the face and taking outdoor activities.

14 Claims, 8 Drawing Sheets

BEAUTY SHEET AND METHOD FOR MANUFACTURING SAME

TECHNICAL FIELD

The present invention relates to a cosmetic sheet that is melted by moisture such as water when adhering to the skin so that nutrients are effectively absorbed onto the skin, and a method of manufacturing the same.

BACKGROUND ART

Conventional general cosmetic sheets have been manufactured to contain essence including nutrients such as natural extracts, proteins, and vitamins on a nonwoven fabric so as to have functions such as whitening, wrinkle reduction, water supply, relief from skin troubles, allowance of skin elasticity, and antibiotics.

However, since the conventional cosmetic sheets are manufactured on the basis of a nonwoven fabric, sufficient adhesion is not achieved at the interface contacting the skin, and thus effective ingredients cannot be sufficiently transferred to the deep part of the skin. In addition, an excessive amount of essence has been added to improve adhesive strength or power with respect to the skin.

Therefore, when a user makes an action actively with a conventional cosmetic sheet attached to the skin, the cosmetic sheet may fall or flow down use due to the self-weight of the cosmetic sheet itself and the excessive essence may flow out, to thus result in uncomfortable and unpleasant feeling and also cause a loss of the essence. In addition, wearing a cosmetic sheet may often make it difficult for a wearer to take daily activities, and thus the wearer may have to lie down during the time of wearing the cosmetic sheet.

In order to overcome such disadvantages, hydrogel cosmetic sheets have recently been widely used. Since the hydrogel cosmetic sheet is excellent in the feeling of fit, a wearer who wears the hydrogel cosmetic sheet may perform daily activities, but the hydrogel cosmetic sheet is so thick to cause limited adhesion and to result in inconveniences of having to remove the hydrogel cosmetic sheet separately after the lapse of the wearing time.

In recent years, research on electrospinning is being actively conducted as a method of forming nanofibers having a diameter of less than 1 μm. The nanofibers produced by the electrospinning method are formed in a laminate structure having a three-dimensional pore structure at the same time of manufacture, and thus can be applied to various fields including industrial and medical fields such as various filter materials, ultra-light functional clothes utilizing moisture permeability and water resistance, biomedical materials using pore characteristics and large surface areas, and inorganic materials and carbon materials through post-processing.

In particular, in the field of cosmetics, nanofibers can provide much larger skin contact areas than conventional nonwoven fabrics, and can be spun at room temperature and atmospheric pressure. Accordingly, various functional materials are mixed with a spinning solution, and the spinning solution mixed with the various functional materials is spun, to then be manufactured in the form of nanofibers mounted with the functional materials at the same time of spinning.

As disclosed in Korean Patent Application Publication No. 10-2011-080066, a conventional cosmetic sheet has been proposed in which a double-layered nanofiber layer is formed on a nonwoven fabric, and the double-layered nanofiber layer is surface-treated with plasma. However, this technology includes a process of making a composite of the nanofiber layer on the nonwoven fabric and a secondary process such as a plasma treatment, to thus cause not only a problem of increasing a process cost, and but also cause inconveniences in wearing the cosmetic sheet and making an action due to the addition of the nonwoven fabric.

In addition, a process such as lamination, thermal bonding, or ultrasonic bonding using a chemical adhesive or the like is required to make a composite of the nonwoven fabric and the nanofiber layer. When the adhesive or the like is not used, peeling between the nonwoven fabric and the nanofiber layer may happen due to the functional essence or moisture.

Furthermore, the nanofibers of the double-layered structure are spun in the form of a core/shell, in which the core portion is made of polyurethane or the like, and the shell portion contacting the skin is made of biodegradable polymers to minimize the trouble with the skin. However, in the case that 100% of the residual solvent is not removed due to the use of the toxic solvent, there is a problem of secondary contamination by the residual solvent.

Particularly, since most of the biodegradable polymers used in the conventional art are required to be hydrophilized through a plasma treatment due to the hydrophobic properties of the biodegradable polymers, there may have problems of causing an increase in the process cost as well as causing deterioration of the functional material.

DISCLOSURE

Technical Problem

Accordingly, an object of the present invention is to provide a cosmetic sheet in which an effective ingredient is melted by moisture and absorbed into the skin, by using a nanofiber web obtained by electrospinning a water-soluble polymer and a functional material together, and a method of manufacturing the same.

Another object of the present invention is to provide a cosmetic sheet capable of controlling a dissolving rate at which a water-soluble polymer is melted by moisture or mist, by controlling a crosslinking density of the water-soluble polymer thereby controlling a delivery rate at which an effective ingredient is delivered to the skin according to properties of the effective ingredient, and a method of manufacturing the same.

Still another object of the present invention is to provide a cosmetic sheet which is obtained by laminating a cosmetic layer melted by moisture and a moisture retaining layer which is resistant to moisture to thereby prevent moisture from drying out during the time the cosmetic layer is absorbed into the skin, when wearing the cosmetic sheet on the face and taking outdoor activities, and a method of manufacturing the same.

Yet another object of the present invention is to provide an easy-to-use cosmetic sheet in which a cosmetic layer is melted by moisture, and the cosmetic layer and a moisture retaining layer are adhered to each other by moisture, so that the moisture retaining layer is separated from the face when the cosmetic layer is melted by moisture, during wearing the cosmetic sheet on the face and taking outdoor activities, and a method of manufacturing the same.

Technical Solution

In order to achieve the above object, the present invention provides a cosmetic sheet comprising: a cosmetic layer configured in the form of a nanofiber web and melted by moisture by electrospinning a water-soluble polymer material and a functional material together; and a moisture retaining layer separably attached to the cosmetic layer and retaining the moisture of the cosmetic layer when wearing the cosmetic layer on the face and performing outdoor activities.

The moisture retaining layer may be formed of a polyurethane film.

The moisture retaining layer may be attached to the cosmetic layer by moisture and have a form capable of being separated from each other.

A design print layer that makes an aesthetic design may be integrally formed on the moisture retaining layer.

The moisture retaining layer may include an ultraviolet blocking agent so as to have an ultraviolet blocking property.

The cosmetic layer is prepared by electrospinning a spinning solution in which a water-soluble polymer material, a functional material and a crosslinking agent are dissolved together in a solvent to form nanofibers having a diameter of less than 1 µm and accumulating the nanofibers to form nanofiber webs having micropores in which a basis weight of the nanofibers is set in the range of 10-50 gsm (grams per square meter), and when adhering the nanofibers to the skin, the nanofiber webs are slowly dissolved by moisture and absorbed into the skin while being removed.

The water-soluble polymer material may include one or a mixture of two or more selected from polymer materials including polyvinyl alcohol (PVA), polyvinyl pyrrolidone (PVP), polyethylene oxide (PEO), carboxyl methyl cellulose (CMC), starch, polyacrylic acid (PAA) and hyaluronic acid.

The functional material may comprise one or a mixture of two or more selected from water-soluble collagen, vegetable platinum, tocopherol, xylitol and plant extract.

The solvent may be water or alcohol, or a mixed solvent thereof.

The crosslinking agent or co-crosslinking agent may be formed of at least one selected from para-toluene sulfonic acid (TSA), polyurea-co-formaldehyde, tri-methylpropane trimethacrylate (TMPTMA), divinylbenzene (DVB), N-(1-hydroxy-2,2-dimethoxyethyl) acrylamide, N, N.-methylenebisacrylamide, ethylene glycol diacrylate, di (ethylene glycol) diacrylate, boric acid, and glutaraldehyde.

The cosmetic sheet may be used as a nasal pack.

The cosmetic sheet may be used as an eye patch attached under the eyes to remove undulations such as eye wrinkles and dark circles.

A release film may be detachably attached to the cosmetic layer when the cosmetic sheet is attached to the skin, and a separation knob for easily separating the cosmetic sheet or the release film from each other may be formed in the cosmetic sheet or the release film.

The moisture retaining layer may be provided with a separating knob for easily separating the moisture retaining layer and the cosmetic layer from each other.

A method of manufacturing a cosmetic sheet according to the present invention comprises the steps of: electrospinning a spinning solution prepared by dissolving a water-soluble polymer material, a functional material, and a crosslinking agent in water, alcohol or a mixed solvent thereof to form a cosmetic layer in a nanofiber web form having micropores; crosslinking the cosmetic layer so that the cosmetic layer is slowly dissolved and absorbed by the skin; and laminating an inorganic porous type moisture retaining layer on one surface of the cosmetic layer.

Advantageous Effects

As described above, the cosmetic sheet according to the present invention uses a nanofiber web obtained by electrospinning a water-soluble polymer and a functional material together, whereby an effective ingredient is absorbed into the skin while being melted by moisture.

The cosmetic sheet according to the present invention may control a dissolving rate at which a water-soluble polymer is melted by moisture or mist, by controlling a crosslinking density of the water-soluble polymer thereby controlling a delivery rate at which an effective ingredient is delivered to the skin according to properties of the effective ingredient.

The cosmetic sheet according to the present invention may be obtained by laminating a cosmetic layer melted by moisture and a moisture retaining layer which is resistant to moisture to thereby prevent moisture from drying out during the time the cosmetic layer is absorbed into the skin, when wearing the cosmetic sheet on the face and taking outdoor activities.

It is easy to use the cosmetic sheet according to the present invention since a cosmetic layer is melted by moisture, and the cosmetic layer and a moisture retaining layer are adhered to each other by moisture, so that the moisture retaining layer is separated from the face when the cosmetic layer is melted by moisture, during wearing the cosmetic sheet on the face and taking outdoor activities.

In addition, since the cosmetic sheet according to the present invention uses a nanofiber web, even when a relatively expensive functional material is contained, a cosmetic effect can be maximized even if only a small amount of the functional material is included because of a large specific surface area of the nanofiber web.

BEST MODE

Hereinafter, embodiments of the present invention will be described in detail with reference to the accompanying drawings. The sizes and shapes of the components shown in the drawings may be exaggerated for clarity and convenience. In addition, terms defined in consideration of the configuration and operation of the present invention may vary depending on the intention or custom of the user, the operator, and the like. Definitions of these terms should be based on the content of this specification.

Figure 1:
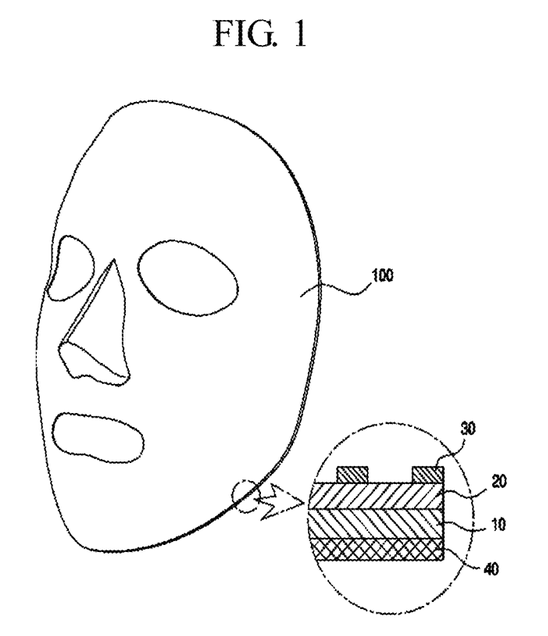
FIG. 1 is a perspective view of a cosmetic sheet according to a first embodiment of the present invention, with a partial cross-sectional view of a portion of the cosmetic sheet.
Figure 2:
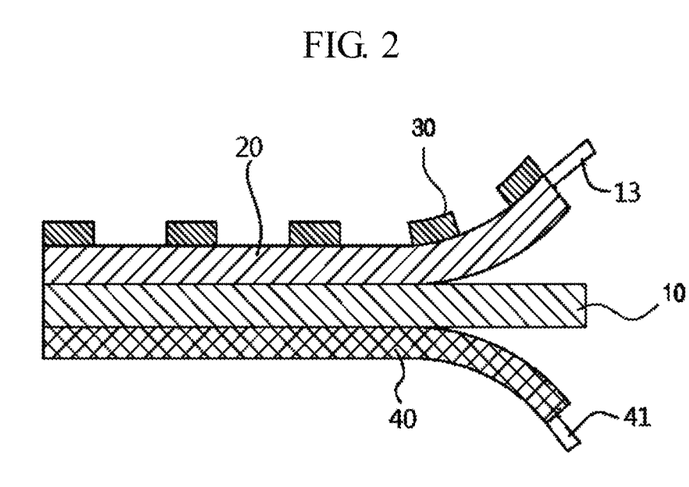
FIG. 2 is a cross-sectional view showing a cosmetic sheet according to a second embodiment of the present invention is attached to a face.

FIG. 1 is a perspective view of a cosmetic sheet according to a first embodiment of the present invention, with a partial cross-sectional view of a portion of the cosmetic sheet, and FIG. 2 is a cross-sectional view showing a cosmetic sheet according to a second embodiment of the present invention is attached to a face.

Referring to FIGS. 1 and 2, a cosmetic sheet 100 according to an embodiment of the present invention includes: a cosmetic layer 10 formed by electrospinning a water-soluble polymer and a functional material together in the form of a nanofiber web and melted by moisture; and a moisture retaining layer 20 which is laminated on the cosmetic layer 10 and is formed of a substance resistant to moisture and has a moisture retaining function.

A release film 40 is detachably attached to the cosmetic layer 10 in which the release film 40 is detached from the cosmetic layer 10 when the cosmetic sheet 100 is attached to the skin. As shown in FIG. 2, the cosmetic layer 10 or the release film 40 may be provided with a separation knob 41 for easily separating the release film 40 from the cosmetic layer 10. Preferably, a separating knob 13 may be also formed on a moisture retaining layer 20.

Figure 3:
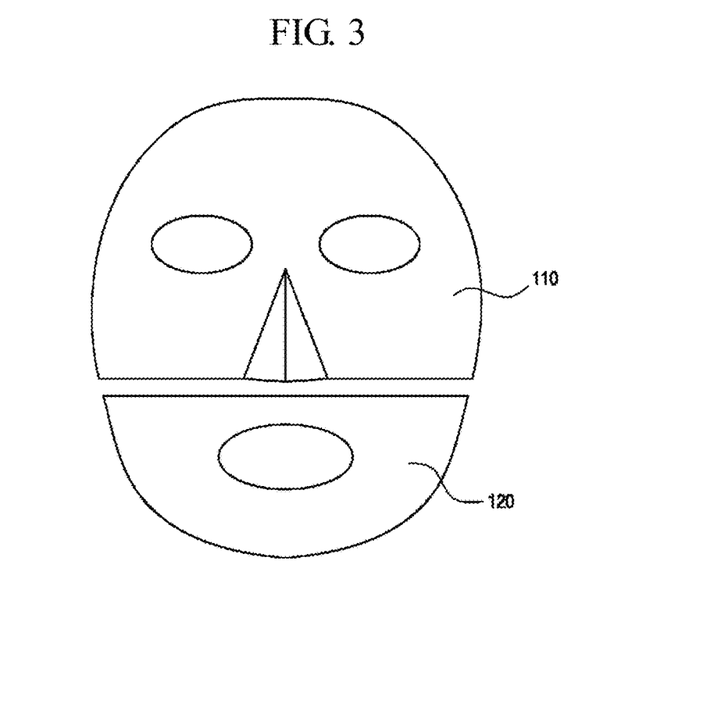
FIG. 3 is a front view showing a cosmetic sheet according to a third embodiment of the present invention is attached to a face.

The cosmetic sheet 100 may be formed in the form of a single mask pack attached to the entire face as shown in FIG. 1, or may be formed in the form of a first cosmetic pack 110 and a second cosmetic pack 120 that are partially cut to fit on the face size as shown in FIG. 3.

Figure 4:
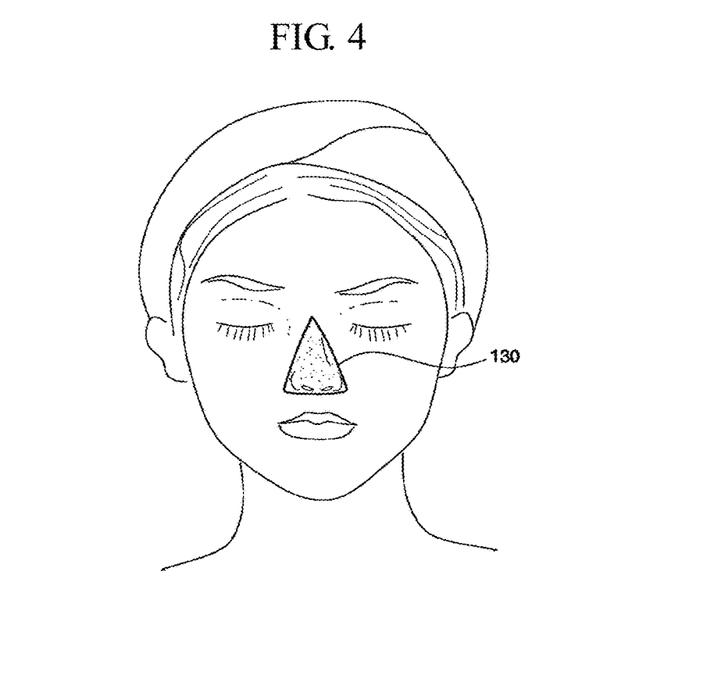
FIG. 4 is a front view showing a cosmetic sheet according to a fourth embodiment of the present invention is attached to a face.

In addition, the cosmetic sheet 130 may be attached to the outer surface of the nose so as to be wrapped around the nose, to thus remove sebum of the nose and perform a cosmetic function for the nose, as shown in FIG. 4.

Figure 5:
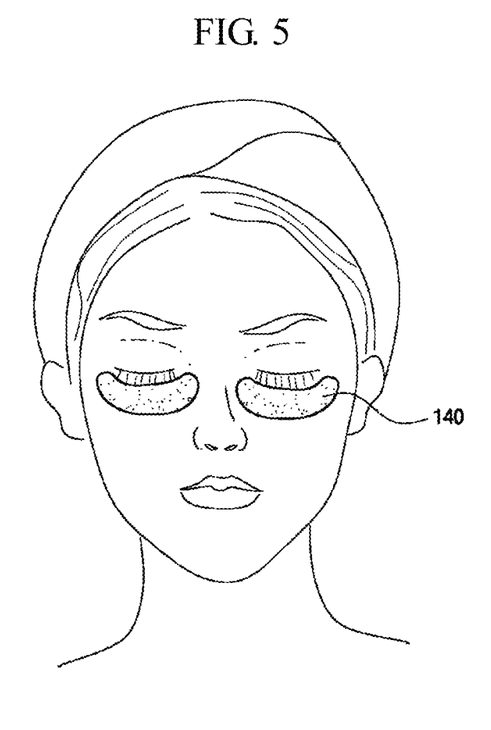
FIG. 5 is a front view for illustrating a manufacturing process of a cosmetic sheet according to the present invention.

In addition, as shown in FIG. 5, the cosmetic sheets 140 can be used as eye pads which are attached under the eyes to remove under-eye wrinkles and dark circles.

In addition to these kinds of cosmetic sheets, the cosmetic sheets can be formed into various shapes that can be used as cosmetic packs.

Referring back to FIGS. 1 and 2, the moisture retaining layer 20 is preferably formed of a polyurethane film that is provided in a state where the outer appearance is luxurious and that is capable of providing a moisture retaining function for preventing the moisture of the cosmetic layer from drying quickly when the outdoor activities are performed in a state where the cosmetic sheet is attached onto the skin.

In addition, the moisture retaining layer 20 may include an ultraviolet screening agent so as to block the ultraviolet rays during performing outdoor activities in a state where the cosmetic sheet 100 is attached to the skin.

A design pattern layer 30 that can beautify the design may be integrally formed with the surface of the moisture retaining layer 20.

The moisture retaining layer 20 is detachably attached to the cosmetic layer 10. That is, when the moisture retaining layer 20 is used only indoors, the moisture retaining layer 20 is detached from the cosmetic layer 10, and only the cosmetic layer is attached to the face. When the cosmetic sheet is attached to the skin and outdoor activities are performed, the cosmetic sheet on which the moisture retaining layer is detachably attached is used to then be attached to the face.

The moisture retaining layer 20 may be provided with a separation knob 13 for easily separating the moisture retaining layer 20 from the cosmetic layer 10 when separating the cosmetic layer 10 and the moisture retaining layer 20 from each other.

The moisture retaining layer 20 can maintain the state of being attached to the cosmetic layer 10 by the moisture of the cosmetic layer 10. Therefore, when the cosmetic layer 10 is completely absorbed into the face, the moisture retaining layer 20 is separated from the face.

The cosmetic sheet 100 according to the present invention is provided with the moisture retaining layer 20 to prevent the moisture from drying quickly while the effective ingredient is absorbed into the skin when the outdoor activities are performed with the cosmetic sheet 10 attached.

That is, when performing the outdoor activities such as a bicycle, a jogging, or a walk, a protective cover is put on the face or an ultraviolet screening agent is applied to the face, to protect the face from ultraviolet rays of the sun.

The cosmetic layer 10 is prepared by dissolving a hydrophilic polymer and a functional material in a solvent to prepare a spinning solution, then electrospinning the spinning solution to form nanofibers having a fiber diameter of less than 1 μm, and accumulating the nanofibers, in the form of a nanofiber web having micropores.

The spinning method that may be applied for the present invention may employ any one of general electrospinning, air-electrospinning (AES), electrospray, electrobrown spinning, centrifugal electrospinning, and flash-electrospinning.

The cosmetic layer 10 may be spun by blending the water-soluble polymer alone or in combination of two or more kinds of the water-soluble polymers. The solvent may employ water, alcohol, or the like having compatibility with the polymer to then be used, alone or in combination thereof.

When preparing the cosmetic layer 10, a crosslinking agent is mixed with the spinning solution for crosslinking the water-soluble polymer. Generally, when dissolving a polymer material, it is preferable to prepare a spinning solution while heating and stirring the polymer material, cooling the spinning solution to room temperature, and then adding a crosslinking agent so that the crosslinking agent is added to the spinning solution in such a range that a crosslinking reaction does not occur.

Therefore, when preparing the cosmetic layer 10 of the present invention, it is preferable that the addition of the crosslinking agent during the preparation of the spinning solution is performed in the final step after dissolving the water-soluble polymer in water or alcohol and adding the functional material in the dissolved result. The content of the crosslinking agent to be added is preferably in the range of 0.1 wt % to 2 wt %, with respect to the polymer. The crosslinking can be performed by a method such as hot air blowing, heat treatment calendering, UV irradiation, etc. The content and time of the crosslinking agent can be adjusted according to the purpose of use.

The water-soluble polymer material may be electrospun and may include synthetic polymers or natural polymers. The synthetic polymers or natural polymers may be used alone or in combination thereof, but any polymers that may be dissolved in water or alcohol to form nanofibers by electrospinning are not particularly limited.

Examples of such water-soluble polymer materials may include one selected from polyvinyl alcohol (PVA), polyvinyl pyrrolidone (PVP), polyethylene oxide (PEO), carboxyl methyl cellulose (CMC), starch, polyacrylic acid (PAA), and hyaluronic acid, or a mixture of two or more thereof.

Examples of functional materials may include: ingredients that help skin whitening (arbutin, niacinamide, ascoglucoside, etc.), ingredients that help to improve skin wrinkles (retinol, adenosine, etc.) ingredients that help to block ultraviolet rays (titanium dioxide, and the like). In addition, all the components used in the cosmetic sheet for the purposes of oxidation prevention, skin and hair conditioning, emulsion stability, pH control, antibacterial effects, and the like may be constituted alone or as a mixture thereof.

The functional material may be one selected from the group consisting of water-soluble collagen, vegetable platinum, tocopherol, xylitol, and vegetable extract or a mixture of two or more thereof. Preferably, the functional material is added in an amount of 0.5 wt % to 50 wt % relative to the water-soluble polymer.

The crosslinking agent or co-crosslinking agent may be formed of one selected from para-toluene sulfonic acid (TSA), polyurea-co-formaldehyde, tri-methylpropane trimethacrylate (TMPTMA), divinylbenzene (DVB), N-(1-hydroxy-2,2-dimethoxyethyl) acrylamide, N, N.-methylenebisacrylamide, ethylene glycol diacrylate, di (ethylene glycol) diacrylate, boric acid, and glutaraldehyde, or a mixture of two or more thereof.

The manufacturing process of the cosmetic sheet will be described below.

Preparation of Spinning Solution Containing Hydrophilic Polymer and Functional Material A spinning solution is prepared to form a cosmetic layer by dissolving a hydrophilic polymer at a spinnable concentration in a solvent such as water or alcohol. The concentration of the spinning solution is suitable when maintaining the fibrous morphology during spinning, and the polymer material in the spinning solution (solvent+polymer material) is suitable in the range of about 5 to 70 wt %.

In the case the proportion of the polymer is less than 5 wt %, a drop due to a low concentration is formed rather than forming nanofibers during electrospinning, so that fibers cannot be formed in many cases. Since he content of the polymer is too much when the amount is more than 70 wt %, it is not possible to form nanofibers due to poor spinning. Therefore, it is necessary to prepare a spinning solution in a suitable concentration range in which fibers can be formed depending on the kind of polymer used. In particular, when two or more polymers are blended and spun, the polymer and solvent should be compatible with each other and should be satisfied with conditions that do not cause phase separation and the like. In addition, it is preferable to prepare a spinning solution by mixing one or two kinds of solvents while considering the volatilization of the solvent.

In addition, when preparing a spinning solution by mixing a functional material and a crosslinking agent, it is necessary to prepare the spinning solution by dissolving the polymer material and injecting the functional material and the crosslinking agent at room temperature. When PVA or the like is used as a polymer, heating and stirring are generally carried out in the preparation of a spinning solution. Therefore, when a crosslinking agent is added, a crosslinking reaction may occur and a solid component may be formed without forming a solution.

Formation of Cosmetic Layer

An electrospinning device includes a spinning nozzle for electrospinning a spinning solution, and a collector for accumulating microfine fiber yarns spun from the spinning nozzle to sequentially form a cosmetic layer and a moisture retaining layer.

In this state, a voltage is applied to the spinning nozzle to conduct electrospinning, by using a high voltage generator. The use voltage is a voltage capable of being spun in the range of 2 kV-100 kV.

It is preferable that a discharge amount during spinning should be discharged and spun in the range of 0.01 to 5 cc/hole·min, and the spinning is performed in an environment of a relative humidity of 10 to 90% in a chamber capable of controlling temperature and humidity during spinning. In order to improve handling properties, the basis weight of the nanofiber web is preferably in the range of 10-50 gsm.

The spinning solution is made into ultrafine fiber strands in the spinning nozzle and is spun onto the surface of the release film 40. Ultrafine nanofibers are then accumulated on the surface of the release film 40 to form a cosmetic layer 10 in the form of a nanofiber web having a plurality of pores.

Crosslinking and Thermocompression (Calendering)

In order to control the time that the electrospun nanofiber web is melted by moisture or mist, it is necessary to perform a crosslinking process and a thermocompression process to increase a bonding force between the nanofibers.

The crosslinking is controlled so that the complete crosslinking or the partial crosslinking proceeds to be self-melt over time by moisture, mist, or the like. The crosslinking can be carried out before or after thermo compression or calendering, or can proceed simultaneously with calendering. For partial crosslinking, the type and content of the crosslinking agent in the spinning solution and the time of hot air, heat treatment calendering, and UV irradiation can be adjusted.

In this case, it is preferable to carry out partial crosslinking in the range that the deterioration or destruction of the functional material does not occur, within the range of 80-100° C. for 30 minutes or less, but in the case of the heating and calendering at 150° C., partial crosslinking is carried out for 30 seconds or less, and is preferably executed in the range that the deterioration of the functional material and the partial crosslinking proceeds.

Lamination of Moisture Retaining Layer

A moisture retaining layer is laminated on one side of the cosmetic layer. The moisture retaining layer is formed of a polyurethane film and attached to one surface of the cosmetic layer by moisture contained in the cosmetic layer.

In this case, a polyurethane film having a design pattern layer 20 that can create an aesthetic design may be integrally formed on one surface of the moisture retaining layer 20.

As described above, since the cosmetic layer and the moisture retaining layer are attached to each other by moisture, they can be separated easily and conveniently, and when the cosmetic layer is melted by moisture and disappears, the moisture retaining layer can be separated from the face naturally.

Hereinafter, the present invention will be described in more detail with reference to embodiments. However, the following embodiments are intended to further illustrate the present invention, and the scope of the present invention is not limited by these embodiments.

Embodiment 1

Polyvinyl alcohol (PVA) as a hydrophilic polymer was made to become 25 wt % in water and a primary spinning solution was prepared at 80° C. Water-soluble collagen was added to the prepared spinning solution by 10 wt % relative to PVA and stirred at room temperature to prepare a final spinning solution. The final spinning solution was moved to a spinning pack and electrospinning was carried out in an electrospinning environment such as temperature of 30° C. and relative humidity of 60% under the circumstance that the applied voltage was 25 kV, the distance between the spinning nozzle and a current collector was 20 cm, and the discharge amount was 0.05 cc/hole·min, to thus obtain a nanofiber web.

Figure 6:
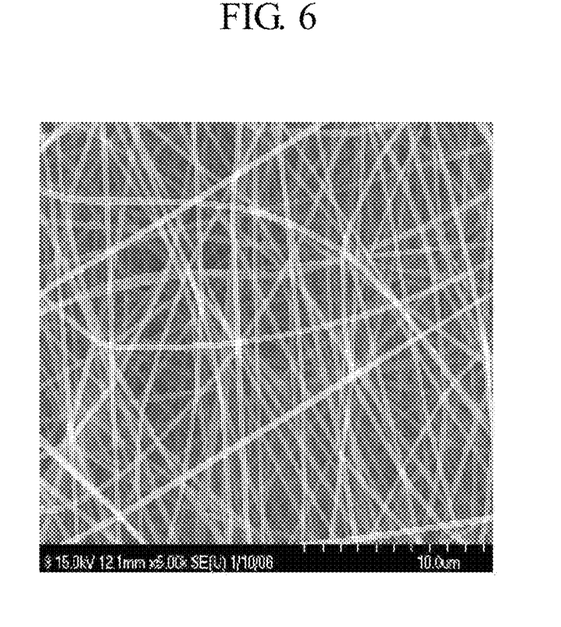
FIG. 6 is a scanning electron micrograph (SEM) image of a PVA nanofiber web prepared according to the present invention.

A scanning electron micrograph (SEM) image of the obtained PVA nanofiber web was shown in FIG. 6, and the distribution of the fiber diameter was about 150-350 nm and the average fiber diameter was about 200 nm. The PVA nanofiber web thus prepared was treated with a hot air furnace at 100° C. for 10 minutes to conduct partial crosslinking.

Embodiment 2

Polyvinyl alcohol (PVA) as a hydrophilic polymer was dissolved in water at 25 wt % and completely dissolved at 80° C. Then, para-toluene sulfonic acid (TSA) as a crosslinking agent and water-soluble collagen as a functional material were added to PVA in an amount of 2 wt % and 5 wt %, respectively, relative to PVA, to thus prepare a spinning solution.

The spinning solution was spun in the same manner as in Embodiment 1 to obtain a PVA nanofiber web containing a crosslinking agent and water-soluble collagen.

Figure 7:
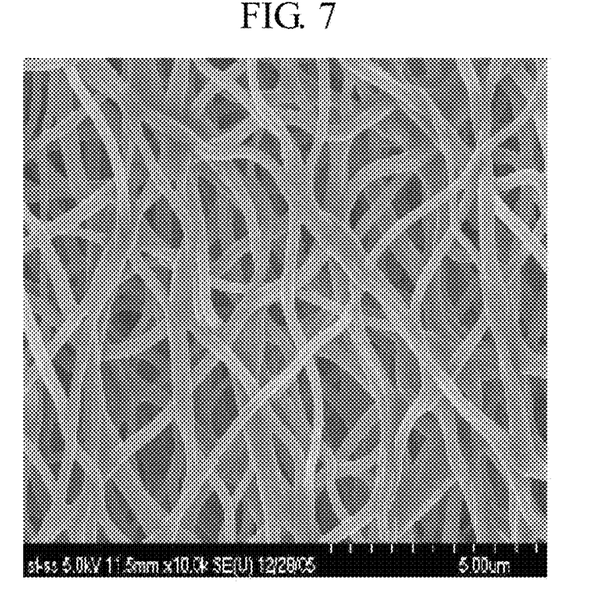
FIG. 7 is a scanning electron micrograph (SEM) image of a fully crosslinked PVA nanofiber web according to an embodiment of the present invention.

The obtained PVA nanofibers were completely crosslinked by treatment with a hot air furnace at 150° C. for 30 minutes, and it was visually confirmed that the surfaces of the crosslinked PVA nanofibers changed from white to yellow as the crosslinking progressed. FIG. 7 shows a scanning electron micrograph (SEM) image of the crosslinked nanofiber web according to the embodiment of the present example. As shown in FIG. 7, it was confirmed that fusion between the fibers occurred by the crosslinking treatment.

Embodiment 3

Polyvinyl pyrrolidone (PVP, K-80) as a hydrophilic polymer was dissolved in a mixed solvent of ethanol and water respectively containing 75 wt % and 25 wt %, to become 15 wt % relative to the mixed solvent, to thus prepare a primary spinning solution. Water-soluble collagen, hyaluronic acid, and vegetable platinum were added to the prepared primary spinning solution in an amount of 5 wt %, respectively, relative to the PVP, and while stirring the primary spinning solution at room temperature, poly (urea-co-formaldehyde) as a crosslinking agent, was added to the primary spinning solution in an amount of 2 wt %, relative to the PVP, to thus prepare a final spinning solution.

The final spinning solution was electrospun in the same manner as in Embodiment 1 to obtain a nanofiber web containing PVP and a functional material. The obtained nanofibers were crosslinked in a hot air furnace at 125° C. for 30 minutes to obtain a PVP crosslinked nanofiber web containing a functional material.

Figure 8A:
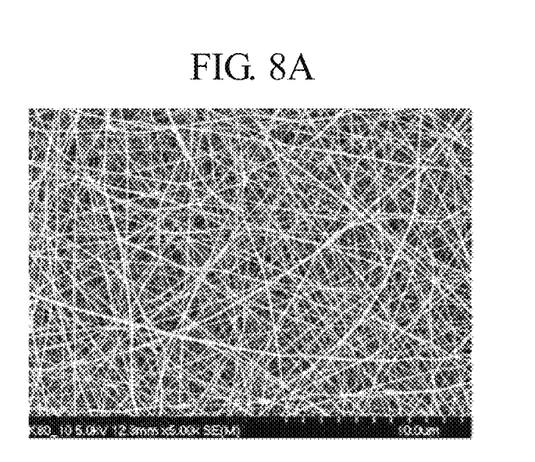
FIG. 8A is a scanning electron microscope (SEM) image of a PVP nanofiber web prepared according to an embodiment of the present invention.
Figure 8B:
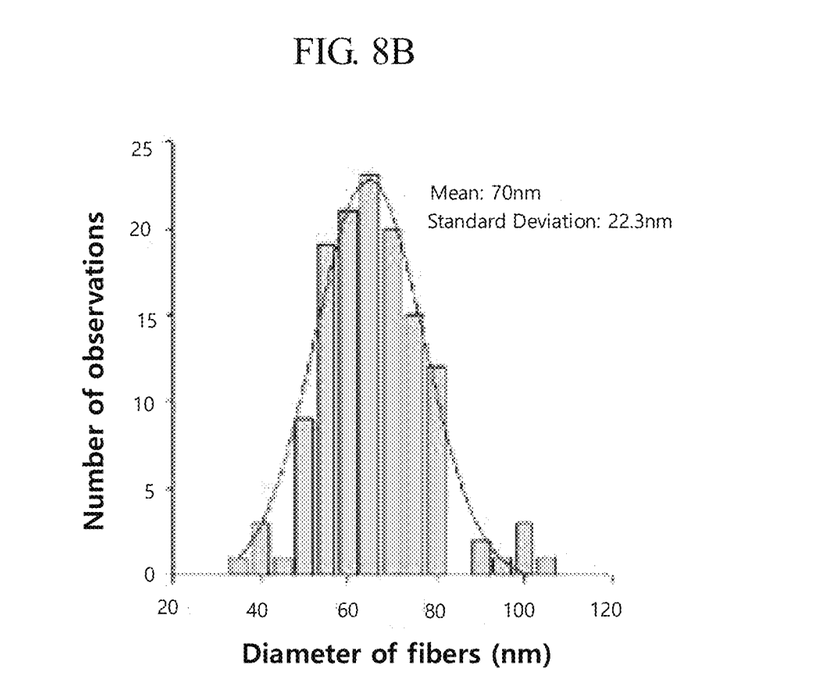
FIG. 8B is a graph showing a diameter distribution of nanofibers of FIG. 8A.

Meanwhile, in the same manner as in Embodiment 1, a PVP single nanofiber web on which a functional material was not mounted was prepared, and a scanning electron microscopic (SEM) image and a diameter distribution of the obtained nanofiber web were shown in FIGS. 8A and 8B, and the average fiber diameter was about 70 nm.

Figure 9:
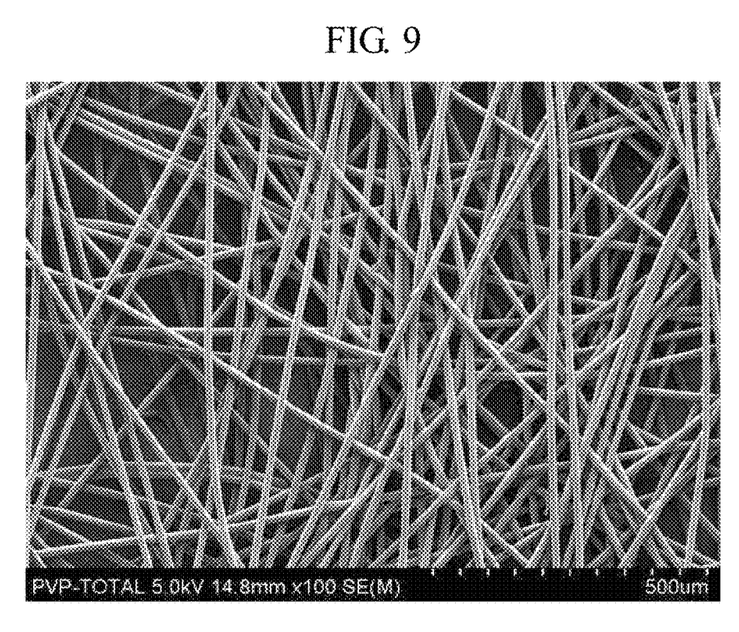
FIG. 9 is a scanning electron micrograph (SEM) image of a PVP nanofiber web loaded with a functional material according to the present invention.

FIG. 9 shows a scanning electron microscope (SEM) image of the PVP on which the functional material is mounted according to an embodiment of the present embodiment, and it can be confirmed that the diameter of the fiber is remarkably increased as compared with the PVP alone.

Embodiment 4

PVA and PVP as hydrophilic polymers were mixed at a ratio of 50:50 wt % in a solvent of water and ethanol at a ratio of 75:25 wt % and stirred at a temperature of 60° C. to prepare a primary spinning solution. The primary spinning solution thus prepared was cooled to room temperature and water-soluble collagen, hyaluronic acid, vegetable platinum and tocopherol as functional materials were mixed in an amount of 3 wt %, respectively, relative to the polymer, to thus prepare a secondary spinning solution.

The crosslinking agent such as TSA was added to the prepared secondary spinning solution in an amount of 1 wt % relative to PVA and stirred to thus prepare a final spinning solution. The same procedure as in Embodiment 1 was followed to conduct electrospinning so that the content of the nanofibers was 20 gsm and calendered for a contact time of 10 seconds using a calender roll heated at 150° C. to thus perform partial crosslinking.

Figure 10A:
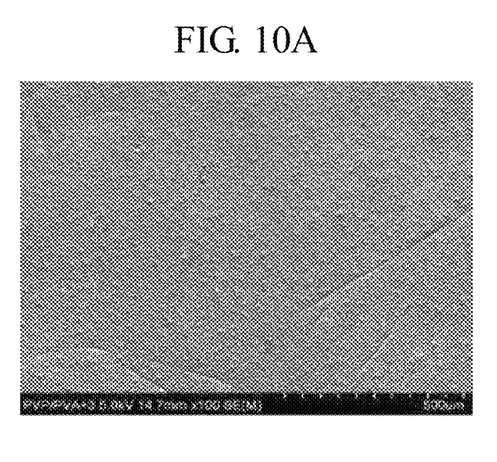
FIG. 10A is a scanning electron micrograph (SEM) image of a PVA/PVP composite nanofiber web prepared according to the present invention, with 100 times magnification, and FIG. 10B with 5,000 times magnification.
Figure 10B:
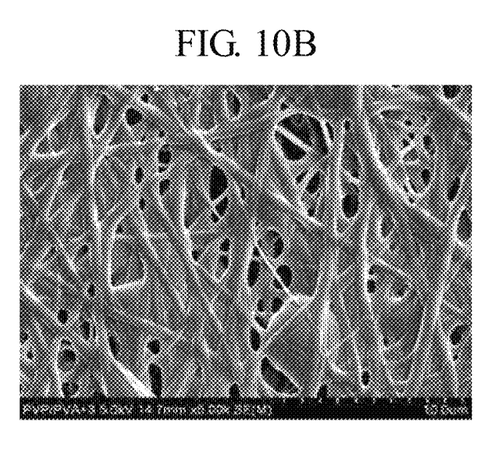

FIG. 10A is a scanning electron micrograph (SEM) image of a PVA/PVP composite nanofiber web prepared according to the present invention, with 100 times magnification, and FIG. 10B with 5,000 times magnification. As shown in FIGS. 10A and 10B, 8 t can be confirmed that fusion between the nanofibers occurred.

Embodiment 5

Figure 11A:
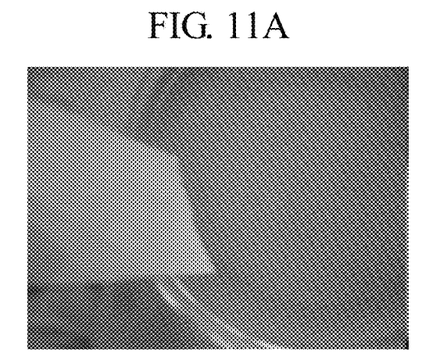
FIG. 11A is a photograph showing a degree of dissolution in water according to a contact time of 3 seconds during heating and calendering of a PVA/PVP nanofiber web prepared according to an embodiment of the present invention, FIG. 11B of 10 seconds, and FIG. 11C of 30 seconds.

The crosslinking degree of the PVA/PVP nanofiber web prepared in Embodiment 4 was measured through calendering. FIG. 11A is a photograph of a PVA/PVP nanofiber web prepared according to a contact time of 3 seconds at a temperature of 150° C., FIG. 11B according to a contact time of 10 seconds, and FIG. 11C according to a contact time of 30 seconds.

Figure 11B:
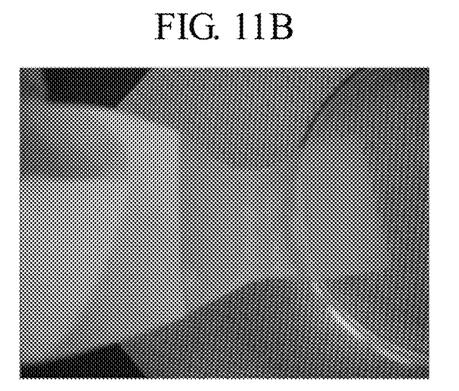
Figure 11C:
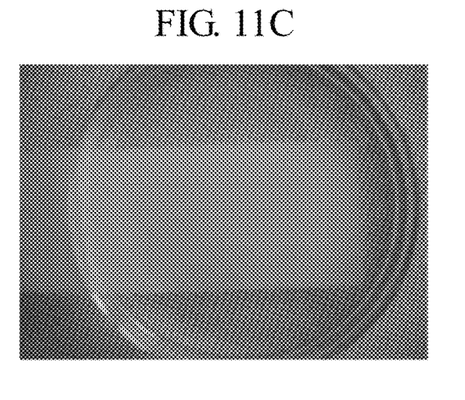

As shown in FIGS. 11A, 11B and 11C, it can be seen that the crosslinking degree increases with an increase in the contact time at the time of calendering the hot plate. As shown in FIG. 11A, when the contact time is short, the crosslinking does not proceed and it is confirmed that the nanofibers are melted simultaneously with a contact to water due to the large specific surface areas of the nanofibers. As shown in FIGS. 11B and 11C, it can be confirmed that when crosslinking proceeds, even if the nanofibers are in contact with water, the nanofibers do not melt immediately and absorb moisture.

From these results, it can be seen that, when using the cosmetic sheet comprising the nanofiber web of the present invention, the skin is moisturized or the mist is dispersed to the skin, and then the cosmetic sheet is attached to the skin, there is an effect that an effective ingredient can be appropriately transmitted to the skin for a desired time through crosslinking.

INDUSTRIAL APPLICABILITY

The cosmetic sheet according to the present invention is attached to the face or skin to allow the functional material to be absorbed into the face or skin, and is formed by laminating a cosmetic layer which is a dry type and melted by moisture and a moisture retaining layer which is resistant to moisture with each other, to prevent moisture from drying out while the cosmetic layer is absorbed into the skin during wearing the cosmetic sheet on the face and performing outdoor activities, and thereby enable a user to perform outdoor activities with the cosmetic sheet attached on the face or skin.

The invention claimed is:

1. A cosmetic sheet comprising:
   a cosmetic layer melted by moisture and configured in the form of a nanofiber web by electrospinning a water-soluble polymer material and a functional material together; and
   a moisture retaining layer separably attached to the cosmetic layer and retaining the moisture of the cosmetic layer when wearing the cosmetic layer on the face and performing outdoor activities,
   wherein the moisture retaining layer is provided with a separating knob for separating the moisture retaining layer and the cosmetic layer from each other, and
   wherein the moisture retaining layer is a polyurethane film.

2. The cosmetic sheet of claim 1, wherein a design print layer that makes an aesthetic design is integrally formed on the moisture retaining layer.

3. The cosmetic sheet of claim 1, wherein the moisture retaining layer includes an ultraviolet blocking agent so as to have an ultraviolet blocking property.

4. The cosmetic sheet of claim 1, wherein the water-soluble polymer material includes one or a mixture of two or more selected from polymer materials including polyvinyl alcohol (PVA), polyvinyl pyrrolidone (PVP), polyethylene oxide (PEO), carboxyl methyl cellulose (CMC), starch, polyacrylic acid (PAA) and hyaluronic acid.

5. The cosmetic sheet of claim 1, wherein the functional material includes an ingredient that helps skin whitening, an ingredient that helps to improve skin wrinkles, an ingredient that helps to block ultraviolet rays, or a combination thereof.

6. The cosmetic sheet of claim 5, wherein:
   the ingredient that helps skin whitening comprises arbutin, niacinamide, ascoglucoside, or a combination thereof;
   the ingredient that helps to improve skin wrinkles comprises retinol, adenosine, or a combination thereof; and
   the ingredient that helps to block ultraviolet rays comprises titanium dioxide.

7. The cosmetic sheet of claim 1, wherein the functional material comprises one or a mixture of two or more selected from water-soluble collagen, vegetable platinum, tocopherol, xylitol and plant extract.

8. The cosmetic sheet of claim 1, wherein the functional material is added in an amount of 0.5 wt % to 50 wt % relative to the water-soluble polymer.

9. The cosmetic sheet of claim 1, wherein:
   the water-soluble polymer material and the functional material are dissolved together with a crosslinking agent in a solvent; and
   the solvent is water or alcohol, or a mixed solvent thereof.

10. The cosmetic sheet of claim 1, further comprising a crosslinking agent or co-crosslinking agent, wherein the crosslinking agent or co-crosslinking agent is formed of at least one selected from para-toluene sulfonic acid (TSA), polyurea-co-formaldehyde, tri-methylpropane trimethacrylate (TMPTMA), divinylbenzene (DVB), N-(1-hydroxy-2, 2-dimethoxyethyl) acrylamide, N,N'-methylenebisacrylamide, ethylene glycol diacrylate, di (ethylene glycol) diacrylate, boric acid, and glutaraldehyde.

11. The cosmetic sheet of claim 1, further comprising a crosslinking agent present in an amount in the range of 0.1 wt % to 2 wt %, with respect to the polymer.

12. The cosmetic sheet of claim 1, wherein the cosmetic sheet is used as a nasal pack.

13. The cosmetic sheet of claim 1, wherein the cosmetic sheet is used as an eye patch attached under the eyes to remove undulations such as eye wrinkles and dark circles.

14. The cosmetic sheet of claim 1, wherein a release film is detachably attached to the cosmetic layer when the cosmetic sheet is attached to the skin, and a separation knob for separating the cosmetic sheet or the release film from each other is formed in the cosmetic sheet or the release film.

* * * * *